(12) United States Patent
Sage

(10) Patent No.: US 7,678,101 B2
(45) Date of Patent: Mar. 16, 2010

(54) LOCKING CATHETER CONNECTOR AND CONNECTION SYSTEM

(75) Inventor: Shahn S. Sage, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 339 days.

(21) Appl. No.: 11/393,089

(22) Filed: Mar. 30, 2006

(65) Prior Publication Data

US 2006/0264814 A1      Nov. 23, 2006

Related U.S. Application Data

(60) Provisional application No. 60/682,948, filed on May 20, 2005.

(51) Int. Cl.
*A61M 25/16* (2006.01)

(52) U.S. Cl. .................................... 604/533

(58) Field of Classification Search ............... 604/250, 604/533–537, 905, 178, 288.01–288.04

See application file for complete search history.

(56) References Cited

U.S. PATENT DOCUMENTS

| | | |
|---|---|---|
| 2,815,227 A | 12/1957 | Cullen et al. |
| 3,447,819 A | 6/1969 | Borsum et al. |
| 3,659,881 A | 5/1972 | Tinsley et al. |
| 3,731,955 A | 5/1973 | Borsum et al. |
| 3,983,203 A | 9/1976 | Corbett |
| 4,013,310 A | 3/1977 | Dye |
| 4,193,616 A | 3/1980 | Sarson et al. |
| 4,310,001 A | 1/1982 | Comben |
| 4,323,065 A | 4/1982 | Kling |
| 4,334,551 A | 6/1982 | Pfister |
| 4,405,163 A | 9/1983 | Voges et al. |
| 4,526,572 A | 7/1985 | Donnan et al. |
| 4,581,012 A | 4/1986 | Brown et al. |
| 4,592,749 A | 6/1986 | Ebling et al. |
| 4,610,468 A | 9/1986 | Wood |
| 4,632,435 A | 12/1986 | Polyak |
| 4,636,204 A | 1/1987 | Christopherson et al. |

(Continued)

FOREIGN PATENT DOCUMENTS

AU        A-21021/83        5/1985

(Continued)

OTHER PUBLICATIONS

U.S. Appl. No. 11/057,666, filed Feb. 14, 2005, Cross.

(Continued)

*Primary Examiner*—Nicholas D Lucchesi
*Assistant Examiner*—Theodore J Stigell
(74) *Attorney, Agent, or Firm*—Mueting, Raasch & Gebhardt, P.A.

(57) ABSTRACT

Connectors, connection systems, and methods for coupling a catheter or catheter assembly to a stem of a medical device. Exemplary connectors may include a seal attached at or near a proximal end of the catheter, and a tubular housing that includes a locking member operable to connect the catheter to the medical device, preferably without the use of tools. Exemplary methods may include: inserting the stem of the device into the housing, wherein the housing is configured to press the seal against the stem, compressing the seal, and moving the locking member into a locked position.

18 Claims, 8 Drawing Sheets

U.S. PATENT DOCUMENTS

| | | | |
|---|---|---|---|
| 4,647,082 A | 3/1987 | Fournier et al. | |
| 4,650,473 A | 3/1987 | Bartholomew et al. | |
| 4,652,258 A | 3/1987 | Drach | |
| 4,673,394 A | 6/1987 | Fenton, Jr. et al. | |
| 4,675,007 A | 6/1987 | Terry | |
| 4,691,943 A | 9/1987 | DeLand et al. | |
| 4,701,159 A | 10/1987 | Brown et al. | |
| 4,704,103 A | 11/1987 | Stöber et al. | |
| 4,723,948 A | 2/1988 | Clark et al. | |
| 4,769,017 A | 9/1988 | Fath et al. | |
| 4,772,276 A | 9/1988 | Wiita et al. | |
| 4,781,185 A | 11/1988 | Kauphusman et al. | |
| 4,786,089 A | 11/1988 | McConnell | |
| 4,810,241 A * | 3/1989 | Rogers | 604/28 |
| 4,820,288 A | 4/1989 | Isono | |
| 4,823,805 A | 4/1989 | Wojcik | |
| 4,834,719 A | 5/1989 | Arenas | |
| 4,850,984 A | 7/1989 | Harris | |
| 4,880,414 A | 11/1989 | Whipple | |
| 4,890,866 A | 1/1990 | Arp | |
| 4,895,561 A | 1/1990 | Mahurkar | |
| 4,895,570 A | 1/1990 | Larkin | |
| 4,915,690 A | 4/1990 | Cone et al. | |
| 4,929,236 A | 5/1990 | Sampson | |
| 4,929,243 A | 5/1990 | Koch et al. | |
| 4,950,232 A | 8/1990 | Ruzicka et al. | |
| 4,950,255 A | 8/1990 | Brown et al. | |
| 4,963,133 A | 10/1990 | Whipple | |
| 4,983,161 A | 1/1991 | Dadson et al. | |
| 4,994,048 A | 2/1991 | Metzger | |
| 4,998,925 A | 3/1991 | Al-Sioufi et al. | |
| 5,000,614 A | 3/1991 | Walker et al. | |
| 5,040,831 A | 8/1991 | Lewis | |
| 5,053,015 A | 10/1991 | Gross | |
| 5,078,699 A | 1/1992 | Haber et al. | |
| 5,127,626 A | 7/1992 | Hilal et al. | |
| 5,129,891 A | 7/1992 | Young | |
| 5,167,647 A | 12/1992 | Wijkamp et al. | |
| 5,178,612 A | 1/1993 | Fenton, Jr. | |
| 5,209,740 A | 5/1993 | Bryant et al. | |
| 5,226,898 A | 7/1993 | Gross | |
| 5,257,622 A | 11/1993 | Hooper et al. | |
| 5,279,597 A | 1/1994 | Dassa et al. | |
| 5,282,790 A | 2/1994 | Clement | |
| 5,290,253 A | 3/1994 | Kira | |
| 5,312,337 A | 5/1994 | Flaherty et al. | |
| 5,314,411 A | 5/1994 | Bierman et al. | |
| 5,330,449 A | 7/1994 | Prichard et al. | |
| 5,354,282 A | 10/1994 | Bierman | |
| 5,360,407 A | 11/1994 | Leonard et al. | |
| 5,360,418 A | 11/1994 | Weilbacher et al. | |
| 5,380,301 A | 1/1995 | Prichard et al. | |
| 5,387,192 A | 2/1995 | Glantz et al. | |
| 5,399,168 A | 3/1995 | Wadsworth, Jr. et al. | |
| 5,405,339 A | 4/1995 | Kohnen et al. | |
| 5,417,672 A | 5/1995 | Nita et al. | |
| 5,423,775 A | 6/1995 | Cannon | |
| 5,429,616 A * | 7/1995 | Schaffer | 604/250 |
| 5,456,671 A | 10/1995 | Bierman | |
| 5,456,676 A | 10/1995 | Nelson et al. | |
| 5,458,581 A * | 10/1995 | Hull | 604/248 |
| 5,466,230 A | 11/1995 | Davila | |
| 5,551,849 A | 9/1996 | Christiansen | |
| 5,562,618 A | 10/1996 | Cai et al. | |
| 5,578,013 A | 11/1996 | Bierman | |
| 5,613,945 A | 3/1997 | Cai et al. | |
| 5,632,729 A | 5/1997 | Cai et al. | |
| 5,637,102 A | 6/1997 | Tolkoff et al. | |
| 5,697,951 A | 12/1997 | Harpstead et al. | |
| 5,702,371 A | 12/1997 | Bierman | |
| 5,743,873 A | 4/1998 | Cai et al. | |
| 5,749,859 A * | 5/1998 | Powell | 604/167.03 |
| 5,792,104 A | 8/1998 | Speckman et al. | |
| 5,797,869 A | 8/1998 | Martin et al. | |
| 5,813,405 A | 9/1998 | Montano, Jr. et al. | |
| 5,827,230 A | 10/1998 | Bierman | |
| 5,830,401 A | 11/1998 | Prichard et al. | |
| 5,833,275 A | 11/1998 | Andersen | |
| 5,865,842 A | 2/1999 | Knuth et al. | |
| 5,913,852 A | 6/1999 | Magram | |
| 5,947,931 A | 9/1999 | Bierman | |
| 5,957,968 A | 9/1999 | Belden et al. | |
| 5,971,958 A | 10/1999 | Zhang | |
| 5,993,437 A | 11/1999 | Raoz | |
| 6,050,949 A | 4/2000 | White et al. | |
| 6,062,902 A | 5/2000 | Buckles et al. | |
| 6,065,075 A | 5/2000 | Ryzin et al. | |
| 6,068,622 A | 5/2000 | Sater et al. | |
| 6,074,379 A | 6/2000 | Prichard | |
| 6,113,572 A | 9/2000 | Gailey et al. | |
| 6,231,548 B1 | 5/2001 | Bassett | |
| 6,234,973 B1 | 5/2001 | Meador et al. | |
| 6,238,374 B1 | 5/2001 | Winkler | |
| 6,245,029 B1 | 6/2001 | Fujita et al. | |
| 6,254,589 B1 | 7/2001 | Raoz | |
| 6,267,754 B1 | 7/2001 | Peters | |
| 6,273,404 B1 | 8/2001 | Holman et al. | |
| 6,290,676 B1 | 9/2001 | Bierman | |
| 6,332,874 B1 | 12/2001 | Eliasen et al. | |
| 6,350,260 B1 | 2/2002 | Goebel et al. | |
| 6,364,841 B1 | 4/2002 | White et al. | |
| 6,402,207 B1 | 6/2002 | Segal et al. | |
| 6,423,053 B1 | 7/2002 | Lee | |
| 6,428,515 B1 | 8/2002 | Bierman et al. | |
| 6,443,903 B1 | 9/2002 | White et al. | |
| 6,453,185 B1 | 9/2002 | O'Keefe | |
| 6,471,689 B1 | 10/2002 | Joseph et al. | |
| 6,506,182 B2 | 1/2003 | Estabrook et al. | |
| 6,508,807 B1 | 1/2003 | Peters | |
| 6,517,115 B1 | 2/2003 | Blivet | |
| 6,517,520 B2 | 2/2003 | Chang et al. | |
| 6,520,546 B2 * | 2/2003 | Szabo | 285/308 |
| 6,554,802 B1 | 4/2003 | Pearson et al. | |
| 6,562,023 B1 | 5/2003 | Marrs et al. | |
| 6,572,555 B2 | 6/2003 | White et al. | |
| 6,579,261 B1 | 6/2003 | Kawamura | |
| 6,607,504 B2 | 8/2003 | Haarala et al. | |
| 6,612,624 B1 | 9/2003 | Segal et al. | |
| 6,641,177 B1 | 11/2003 | Pinciaro | |
| 6,652,489 B2 | 11/2003 | Trocki et al. | |
| 6,673,046 B2 | 1/2004 | Bierman et al. | |
| 6,676,652 B2 | 1/2004 | Mogg | |
| 6,679,528 B1 | 1/2004 | Poder | |
| 6,740,101 B2 | 5/2004 | Houser et al. | |
| 6,749,231 B2 | 6/2004 | LeMay et al. | |
| 6,749,574 B2 | 6/2004 | O'Keefe | |
| 6,796,586 B2 | 9/2004 | Werth | |
| 6,799,991 B2 | 10/2004 | Williams et al. | |
| 6,802,490 B2 | 10/2004 | Leinsing et al. | |
| 6,802,836 B2 | 10/2004 | Bouphavichith et al. | |
| 6,817,995 B1 | 11/2004 | Halpern | |
| 6,827,693 B2 | 12/2004 | White et al. | |
| 6,854,994 B2 | 2/2005 | Stein et al. | |
| 6,893,424 B2 | 5/2005 | Shchervinsky | |
| 6,997,900 B2 | 2/2006 | Westrate et al. | |
| 6,997,919 B2 | 2/2006 | Olsen et al. | |
| 7,014,627 B2 | 3/2006 | Bierman | |
| 7,044,936 B2 | 5/2006 | Harding et al. | |
| 7,344,527 B2 * | 3/2008 | Schweikert et al. | 604/533 |
| 2001/0049519 A1 | 12/2001 | Holman et al. | |
| 2002/0032436 A1 | 3/2002 | Mogg | |
| 2002/0062085 A1 | 5/2002 | White et al. | |
| 2002/0079696 A1 | 6/2002 | Szabo | |
| 2002/0082559 A1 | 6/2002 | Chang et al. | |

| | | | |
|---|---|---|---|
| 2002/0087059 A1 | 7/2002 | O'Keefe | |
| 2002/0151800 A1 | 10/2002 | White et al. | |
| 2002/0188255 A1 | 12/2002 | Bierman et al. | |
| 2003/0004520 A1 | 1/2003 | Haarala et al. | |
| 2003/0018293 A1 | 1/2003 | Tanghoj et al. | |
| 2003/0045912 A1 | 3/2003 | Williams et al. | |
| 2003/0077935 A1 | 4/2003 | Stein et al. | |
| 2003/0097121 A1 | 5/2003 | Jolly et al. | |
| 2003/0135148 A1 | 7/2003 | Dextradeur et al. | |
| 2003/0158539 A1 | 8/2003 | Bouphavichith et al. | |
| 2003/0181849 A1 | 9/2003 | Castellanos | |
| 2003/0199853 A1 | 10/2003 | Olsen et al. | |
| 2003/0209681 A1 | 11/2003 | Leinsing et al. | |
| 2004/0039373 A1 | 2/2004 | Harding et al. | |
| 2004/0044313 A1 | 3/2004 | Nakajima | |
| 2004/0102736 A1 | 5/2004 | Bierman | |
| 2004/0111056 A1 | 6/2004 | Weststrate et al. | |
| 2004/0127854 A1 | 7/2004 | Leinsing et al. | |
| 2004/0158208 A1 | 8/2004 | Hiejima | |
| 2004/0181209 A1 | 9/2004 | Gross | |
| 2004/0181249 A1 | 9/2004 | Torrance et al. | |
| 2004/0204690 A1 | 10/2004 | Yashiro et al. | |
| 2004/0210249 A1 | 10/2004 | Fogarty et al. | |
| 2004/0236312 A1 | 11/2004 | Nistal et al. | |
| 2005/0033371 A1 | 2/2005 | Sommer et al. | |
| 2005/0107739 A1 | 5/2005 | Palma | |
| 2005/0137614 A1 | 6/2005 | Porter et al. | |
| 2005/0143714 A1 | 6/2005 | Hegland et al. | |
| 2005/0251102 A1 | 11/2005 | Hegland et al. | |
| 2005/0253389 A1 | 11/2005 | Schulte | |

FOREIGN PATENT DOCUMENTS

| | | |
|---|---|---|
| DE | 24 56 166 | 8/1976 |
| DE | 90 13 145.2 | 1/1991 |
| EP | 0 332 943 B1 | 9/1992 |
| EP | 0 505 930 A2 | 9/1992 |
| EP | 0 474 266 A2 | 11/1992 |
| EP | 0 474 266 A3 | 11/1992 |
| EP | 0 505 930 A3 | 1/1993 |
| EP | 0 343 910 B1 | 6/1993 |
| EP | 0 559 662 B1 | 9/1993 |
| EP | 0 360 471 B1 | 4/1994 |
| EP | 0 415 665 B1 | 1/1995 |
| EP | 0 505 930 B1 | 6/1996 |
| EP | 0 229 729 B1 | 8/1996 |
| EP | 0 552 180 B1 | 12/1996 |
| EP | 0 504 325 B1 | 1/1997 |
| EP | 0 678 302 B1 | 2/1999 |
| EP | 0 930 083 A2 | 7/1999 |
| EP | 0 930 083 A3 | 10/1999 |
| EP | 1 138 343 A1 | 10/2001 |
| EP | 1 181 946 A1 | 2/2002 |
| EP | 1 186 316 A2 | 3/2002 |
| EP | 0 691 868 B1 | 6/2002 |
| EP | 1 033 146 B1 | 7/2002 |
| EP | 1 219 319 A1 | 7/2002 |
| EP | 1 186 316 A3 | 5/2003 |
| EP | 1 466 645 A2 | 10/2004 |
| EP | 1 501 583 B1 | 5/2006 |
| FR | 2 586 569 | 3/1987 |
| FR | 2 612 784 | 9/1988 |
| FR | 2 750 055 | 8/1998 |
| GB | 2 343 723 | 5/2000 |
| WO | WO 93/05844 A1 | 4/1993 |
| WO | WO 94/21315 A1 | 9/1994 |
| WO | WO 94/21319 A1 | 9/1994 |
| WO | WO 94/23775 A1 | 10/1994 |
| WO | WO 95/19801 A1 | 7/1995 |
| WO | WO 95/19802 A1 | 7/1995 |
| WO | WO 97/25562 A1 | 7/1997 |
| WO | WO 99/53981 A1 | 10/1999 |
| WO | WO 00/13743 A1 | 3/2000 |
| WO | WO 00/24462 A1 | 5/2000 |
| WO | WO 01/91825 A2 | 12/2001 |
| WO | WO 01/91825 A3 | 12/2001 |
| WO | WO 01/91847 A2 | 12/2001 |
| WO | WO 01/91847 A3 | 12/2001 |
| WO | WO 03/002171 A1 | 1/2003 |
| WO | WO 03/020368 A2 | 3/2003 |
| WO | WO 03/070151 A2 | 8/2003 |
| WO | WO 03/090840 A1 | 11/2003 |
| WO | WO 2004/016309 A2 | 2/2004 |
| WO | WO 2004/018015 A2 | 3/2004 |
| WO | WO 2004/016309 A3 | 4/2004 |
| WO | WO 2004/016309 A3 | 6/2004 |
| WO | WO 2004/052272 A2 | 6/2004 |
| WO | WO 2004/060466 A1 | 7/2004 |
| WO | WO 2004/018015 A3 | 9/2004 |
| WO | WO 2004/052272 A3 | 10/2004 |
| WO | WO 2005/030316 A1 | 4/2005 |
| WO | WO 2006/036192 | 4/2006 |

OTHER PUBLICATIONS

U.S. Appl. No. 11/355,627, filed Feb. 16, 2006, Nelson.

* cited by examiner

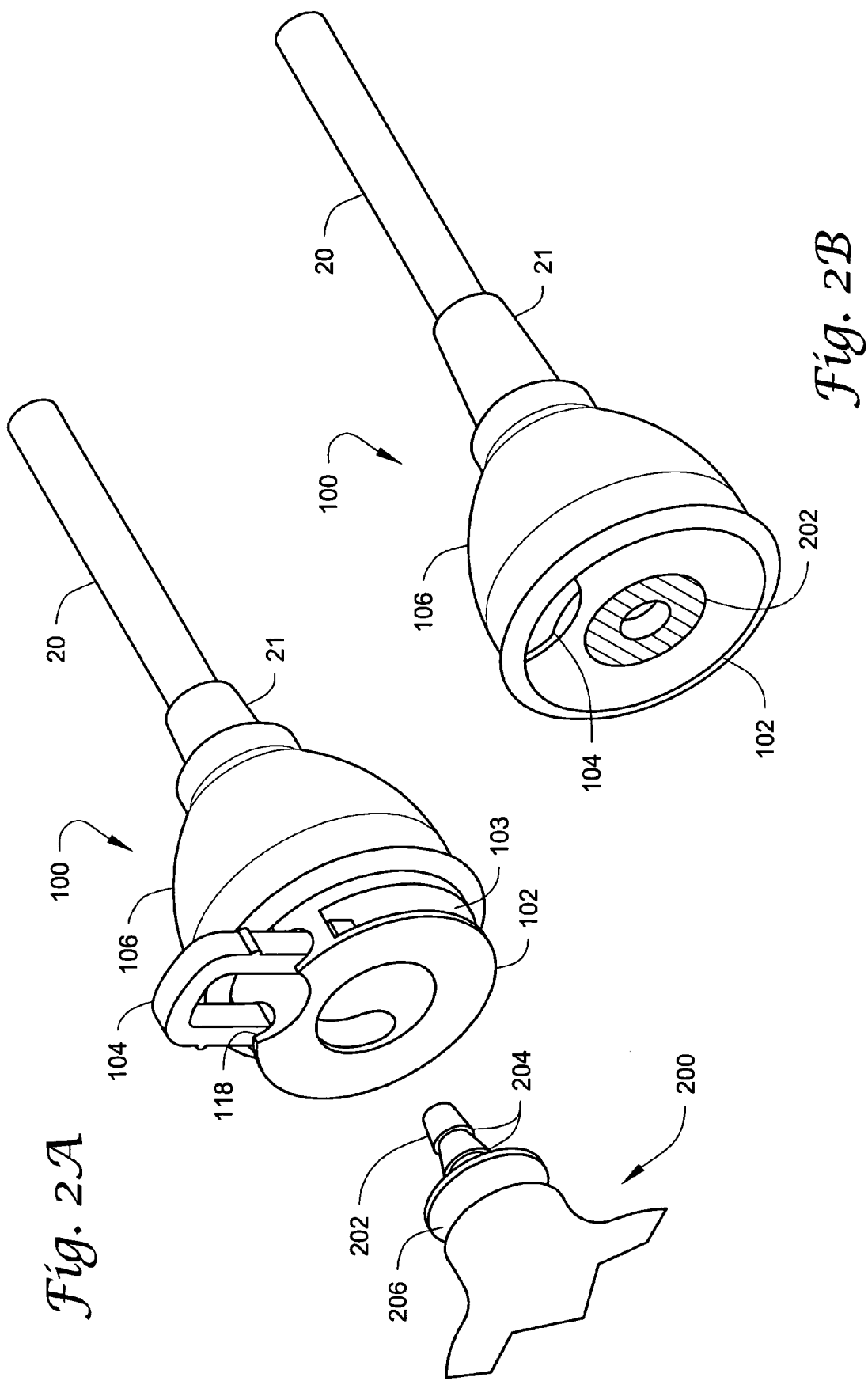

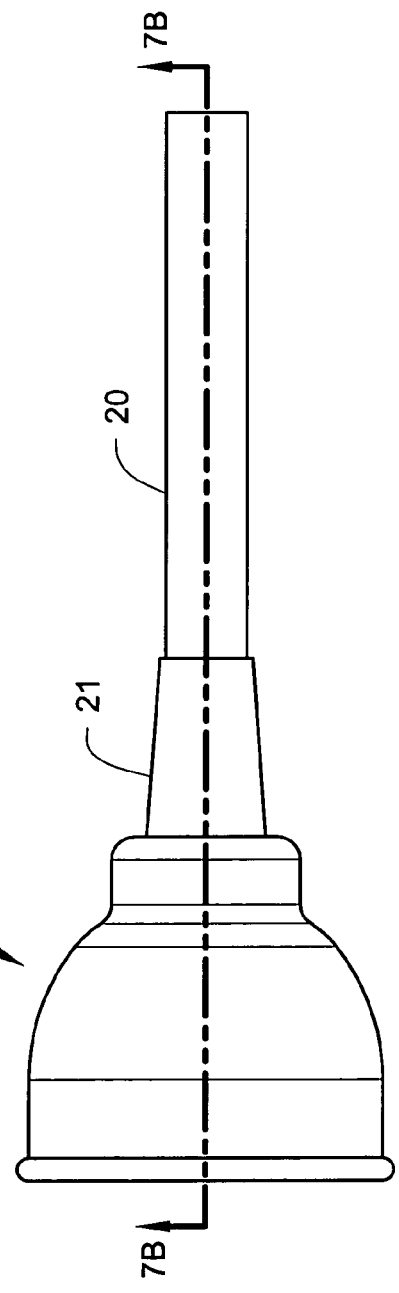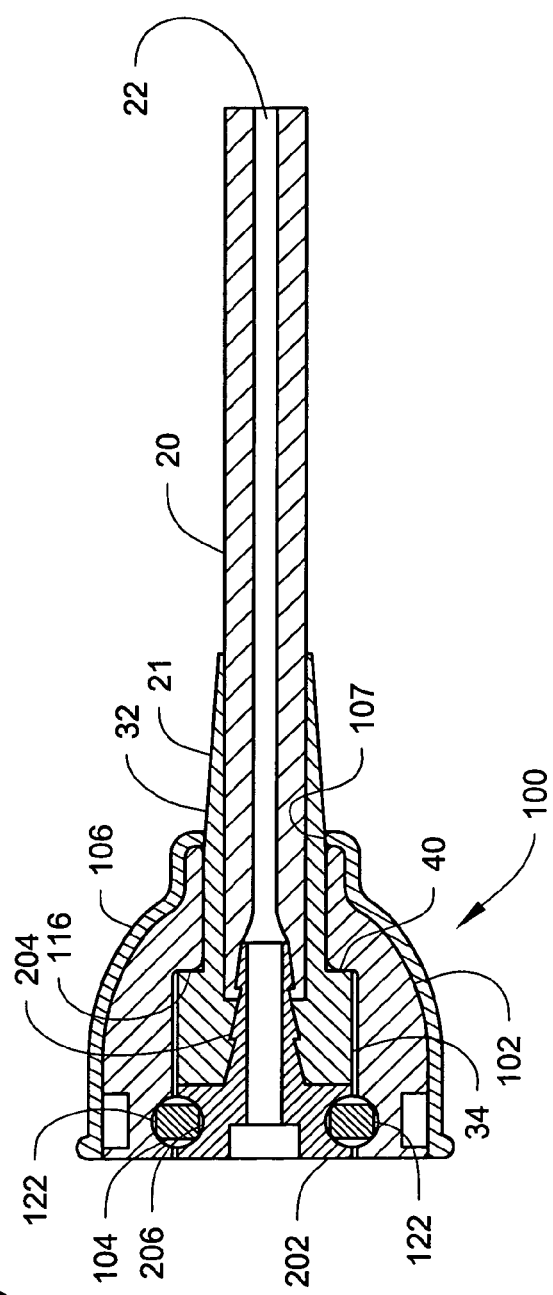

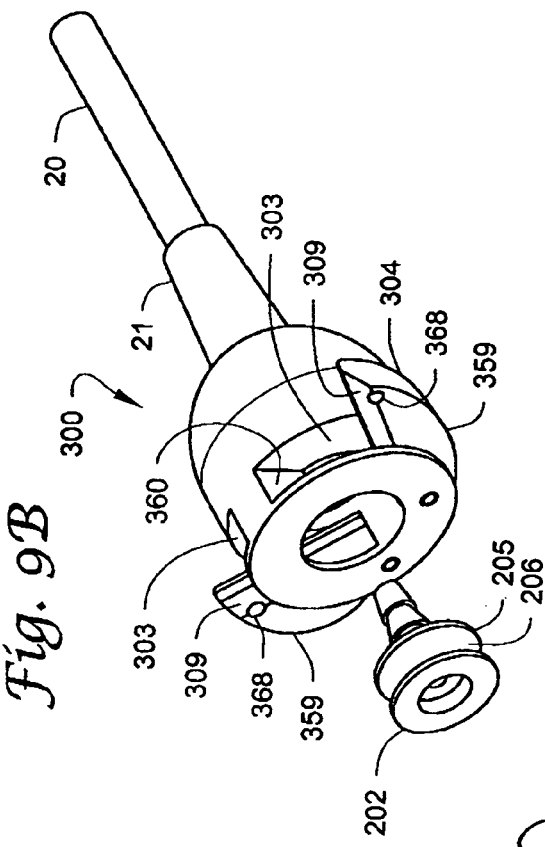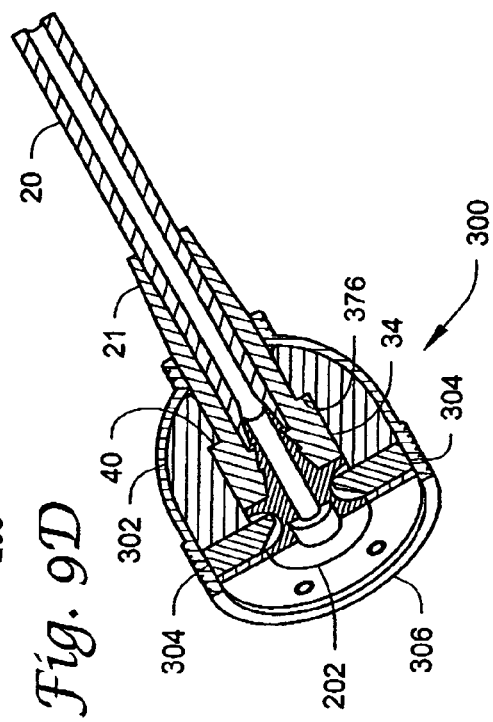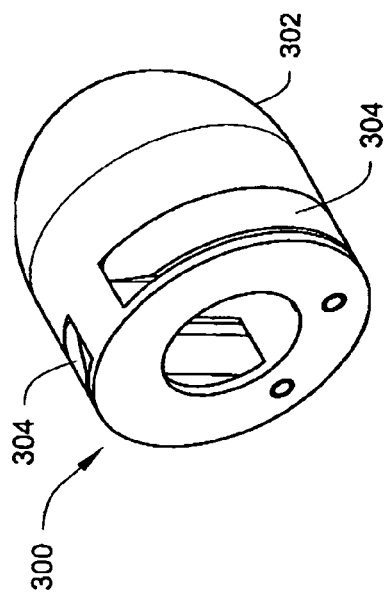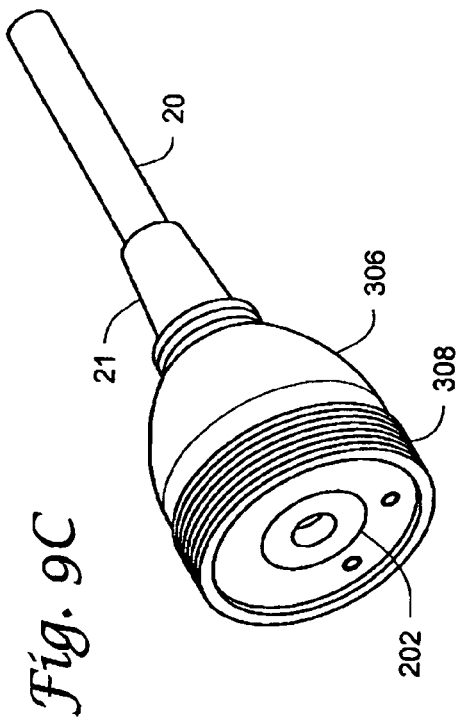

LOCKING CATHETER CONNECTOR AND CONNECTION SYSTEM

RELATED APPLICATIONS

This application claims the benefit of U.S. provisional application Ser. No. 60/682,948, filed May 20, 2005, which is incorporated herein by reference in its entirety.

TECHNICAL FIELD

The present invention relates generally to implantable medical devices and, more particularly, to a locking connector for coupling a catheter to a device such as a drug infusion pump.

BACKGROUND

Treatment of diseases and ailments of the body often benefit from short- or long-term infusion of drugs and/or other fluids. While such medications may be administered extracorporeally, e.g., via transcutaneous injection, many patients benefit from the consistent and repeatable dosage provided by an implanted drug infusion pump. Such pumps may be used in a variety of applications such as control of pain and/or spasticity. They are well-suited to deliver infusate fluids to a targeted delivery site such as an epidural or intrathecal space of the spinal canal, or a particular location within the brain.

Drug infusion pumps are typically implanted subcutaneously, e.g., in the chest or abdominal cavity. The pump may incorporate a chamber to hold the infusate fluid. A needle-penetrable septum may also be provided and is preferably located generally directly beneath the skin. The septum allows drugs or other fluids to be introduced into the infusate chamber by transcutaneous injection. The pump may also include a fluid discharge outlet or stem through which the drug is directed during delivery. The outlet is typically connected to flexible medical tubing, e.g., a catheter, leading to the targeted delivery site.

A secure and leak-free connection of the catheter to the pump outlet is beneficial to ensure correct dosage delivery to the targeted delivery site. If the connection should somehow fail, the intended infusate dosage may not reach the delivery site and, moreover, some (or all) of the infusate could undesirably be dispensed in the vicinity of the pump outlet.

As may be appreciated by those skilled in the art, the connection of the delivery catheter to the discharge outlet may be subjected to various stresses attributable to movement of the patient, as well as to other variables in patient physiology (e.g., weight changes, etc.). These factors may result in separating and/or twisting forces applied at the outlet/catheter connection that, over time, may degrade connection integrity.

Various devices have sought to improve the strength of this connection. For example, raised circular barbs provided on the outlet may resist longitudinal movement of the catheter away from the outlet. In other systems, a suture is provided in place of, or in addition to, the barbs. The sutures may cinch the catheter against the outlet, thereby providing additional resistance to relative catheter motion.

While effective, these catheter connections have drawbacks. For example, barbed stems may not be able to withstand the tensile forces exerted on the catheter due to movements of the patient, or may result in tearing of the catheter in the vicinity of the barb. Moreover, with regard to sutured connections, inherent variability in physician suturing techniques may result in a suture that is incorrectly placed relative to the catheter and connector. As a result, the suture may occlude or otherwise interrupt normal catheter flow. Even when the suture is correctly placed, it may be cinched too tightly—potentially cutting the catheter—or, alternatively, too loosely—potentially reducing the suture's ability to retain the catheter relative to the outlet.

SUMMARY

Embodiments of the present invention provide connectors, methods, and systems for connecting medical tubing to medical devices, such as implantable infusion pumps, that may overcome these and other problems.

In one embodiment, a connector for removably coupling a catheter to a medical device is provided. The connector may include a tubular housing that includes an exterior surface and an interior surface, wherein the interior surface defines a lumen configured to receive both a proximal end portion of the catheter and a stem of the medical device, and further wherein a lock opening extends through the housing between the exterior surface and the interior surface. The connector further includes a locking member that includes a locking leg movable, relative to the lock opening, between an unlocked position, wherein the locking leg is located at or beyond the interior surface, and a locked position, wherein the locking leg protrudes inwardly past the interior surface and into the lumen of the housing.

In another embodiment, a method for coupling a catheter to a medical device is provided. The method includes inserting a stem of the medical device into a tubular housing of a catheter connector, the tubular housing surrounding a seal of the catheter. The method further includes compressing the seal against the stem sufficiently to align two lock openings formed through a wall of the tubular housing with a groove formed in the stem; and moving a locking leg, relative to each of the lock openings, to a locked position, wherein the locking leg extends through the tubular housing and into the groove.

In yet another embodiment of the present invention, a connection system for coupling medical tubing to a stem of a medical device is provided. The system includes a catheter assembly having the medical tubing and a seal attached at or near a proximal end of the tubing. The seal includes: a flange portion having a contact surface, wherein the flange portion is substantially normal to a longitudinal axis of the medical tubing; and a tapered body portion extending from the flange portion of the seal. The connection system further includes a tubular housing including an exterior surface and an interior surface, wherein the interior surface defines a lumen configured to receive both a proximal end portion of the catheter assembly and the stem of the medical device, and further wherein a lock opening extends through the housing between the exterior surface and the interior surface. The connection system additionally includes a locking member that includes a locking leg movable, relative to the lock opening, between an unlocked position, wherein the locking leg is located at or beyond the interior surface, and a locked position, wherein the locking leg protrudes inwardly past the interior surface and into the lumen of the housing. A cover member is also provided and configured to at least partially surround the housing member when the locking member is in the locked position.

The above summary is not intended to describe each embodiment or every implementation of the present invention. Rather, a more complete understanding of the invention will become apparent and appreciated by reference to the following Detailed Description of Exemplary Embodiments in view of the accompanying figures of the drawing.

BRIEF DESCRIPTION OF THE VIEWS OF THE DRAWING

The present invention will be further described with reference to the figures of the drawing, wherein:

FIGS. 1A and 1B illustrate implanted infusion pump systems incorporating a catheter connector in accordance with embodiments of the present invention, wherein: FIG. 1A illustrates a brain infusion system; and FIG. 1B illustrates a spinal infusion system;

FIGS. 2A and 2B illustrate enlarged views of a catheter assembly incorporating a connector in accordance with one embodiment of the invention, wherein: FIG. 2A illustrates the connector in an unlocked configuration; and FIG. 2B illustrates the connector in a locked configuration;

FIGS. 5A-5D illustrate an exemplary housing for use with the connector of FIGS. 2A and 2B, wherein: FIG. 5A is a perspective view; FIG. 5B is a section view taken along lines 5B-5B of FIG. 5C; and FIGS. 5C and 5D are, respectively, top and side elevation views;

FIGS. 6A-6D illustrate a locking member for use with the connector of FIGS. 2A and 2B, wherein: FIG. 6A is a perspective view of the locking member; FIG. 6B is a section view of the connector taken along lines 6C-6C of FIG. 6D but with the locking member shown in an unlocked position relative to a stem of an infusion pump; FIG. 6C is a section view taken along lines 6C-6C of FIG. 6D with the locking member shown in a locked position; and FIG. 6D is a top view of the connector with the locking member shown in the locked position;

FIGS. 7A and 7B illustrate the connector of FIGS. 2A and 2B as it may be connected with the stem of the infusion pump, wherein: FIG. 7A illustrates a top plan view; and FIG. 7B illustrates a section view taken along line 7B-7B of FIG. 7A;

FIGS. 8A-8D illustrate a method for coupling a catheter to the stem of an infusion pump using the connector of FIGS. 2A and 2B, wherein: FIG. 8A illustrates the connector in an unlocked configuration before coupling; FIG. 8B illustrates the connector after coupling and with the locking member in the unlocked position; FIG. 8C illustrates the connector after movement of the locking member to the locked position; and FIG. 8D illustrates the connector in a locked configuration and with a flexible cover member covering the housing; and FIGS. 9A-9D illustrate a catheter assembly incorporating a connector in accordance with an alternative embodiment of the invention, wherein: FIG. 9A is a perspective view of a housing of the connector; FIG. 9B illustrates the connector in an unlocked configuration and proximate the stem of the infusion pump; FIG. 9C illustrates the connector in a locked configuration and with a cover member covering the housing; and FIG. 9D is a section view of the connector of FIG. 9C.

Figure 1A:
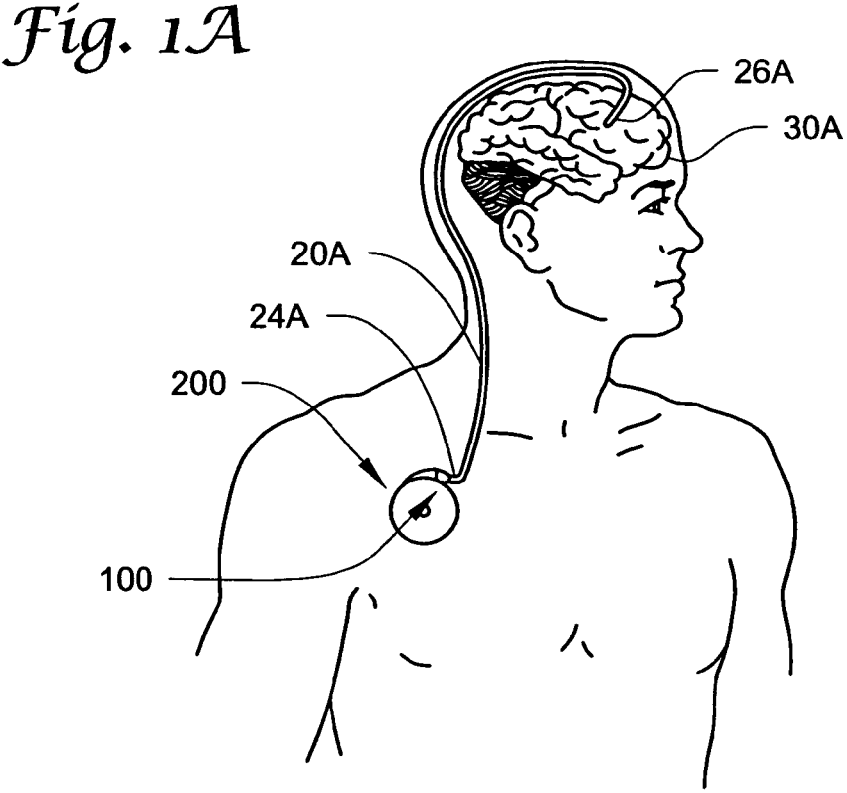

Unless stated otherwise herein, the figures of the drawing are rendered primarily for clarity and thus may not be drawn to scale.

DETAILED DESCRIPTION OF EXEMPLARY EMBODIMENTS

In the following detailed description of illustrative embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention.

In general, embodiments of the present invention are directed to connector apparatus, systems, and methods for connecting medical tubing, e.g., catheters, to a source device such as an implantable drug infusion pump. Preferably, the connectors and methods described herein provide substantially leak-free and secure coupling of the catheter to the pump at implantation, yet may readily permit disconnection and removal by a physician/clinician when desired.

Relative terms such as left, right, forward, rearward, top, bottom, side, upper, lower, horizontal, vertical, and the like may be used herein and, if so, are from the perspective referenced in the particular figure. These terms are used herein only to simplify the description, however, and not to limit the scope of the invention in any way.

It is noted that the term "comprises" and variations thereof do not have a limiting meaning where these terms appear in the accompanying description and claims. Moreover, unless otherwise specified, "a," "an," "the," "one or more," "at least one," and the like are used interchangeably herein and mean one or more than one.

Figure 1B:
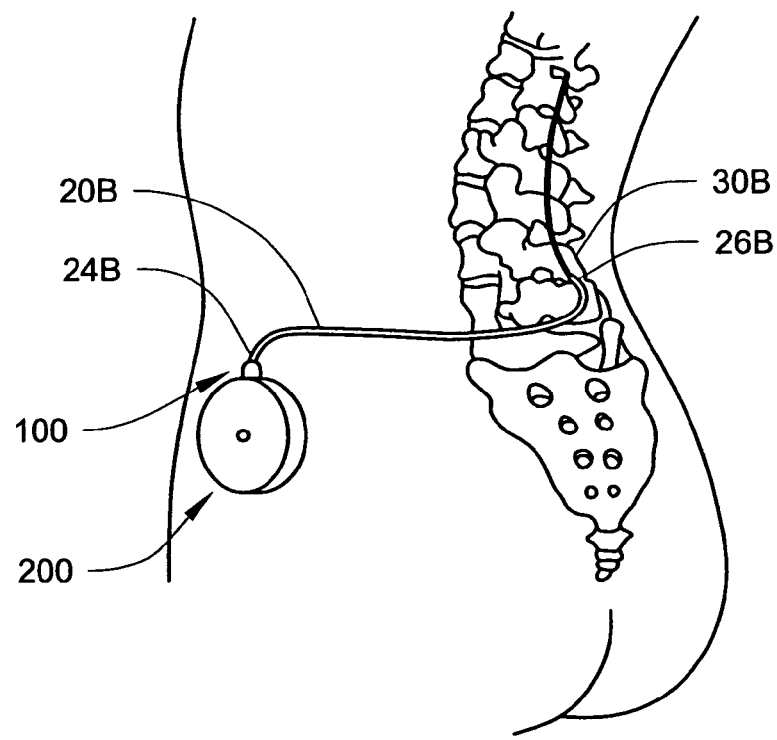

FIGS. 1A and 1B illustrate exemplary implantable infusion systems that may utilize a connector and method in accordance with embodiments of the present invention (or, alternatively, utilize a connector similar to that disclosed in U.S. patent application Ser. No. 11/355,627, filed Feb. 16, 2006, entitled SQUEEZE-ACTUATED CATHETER CONNECTOR AND METHOD, which is incorporated herein by reference in its entirety). FIG. 1A illustrates an implantable drug infusion pump 200 (e.g., an ISOMED or SYNCHROMED infusion device produced by Medtronic, Inc. of Fridley, Minn., USA) configured to deliver an infusate drug to a specific location within the brain 30A. A catheter 20, e.g., catheter 20A, may include a proximal end 24A coupled to the pump 200, and a distal end 26A positioned near the targeted delivery site in the brain 30A. A connector 100 in accordance with one embodiment of the present invention may be used to couple the catheter 20A to the pump 200.

FIG. 1B illustrates another exemplary infusion system wherein a distal end 26B of a catheter, e.g., catheter 20B, is positioned within a spinal canal 30B of the patient. The proximal end 24B is, once again, coupled to the pump 200 with a connector in accordance with an embodiment of the present invention, e.g., the connector 100.

While the exact size and construction of the catheter 20 may certainly vary without departing from the scope of the invention, it may, in one embodiment, be extruded silicone tubing with an undeflected outer diameter of, e.g., about 1 to about 3 millimeters (mm). Other exemplary catheter materials may include polyurethane and co-extrusions such as silicone/polyurethane.

FIGS. 2A and 2B illustrate enlarged perspective views of one embodiment of the connector 100 and a portion of the pump 200. The pump 200 may include a port or stem 202 to which the catheter 20 attaches and through which infusate from the pump is delivered. The stem 202 may form a tapered cylinder having raised barbs 204 thereon (yielding a "Christmas tree" shape) to better engage an inner surface of the catheter. FIG. 2A illustrates the connector 100 detached from the pump 200, and in an unlocked configuration, while FIG. 2B illustrates the connector attached to the pump (shown in section for clarity) and in a locked configuration with an optional cover in place. The proximal end of the catheter 20

Figure 4:
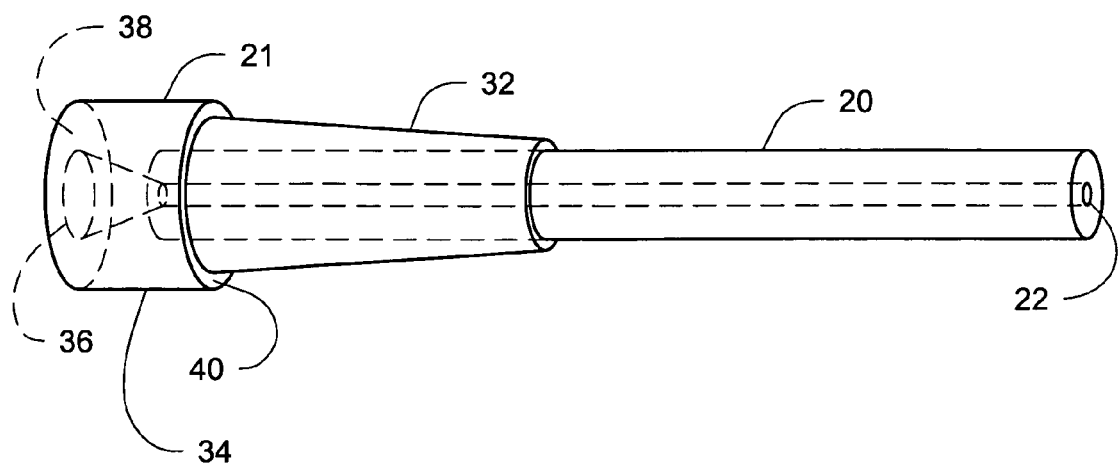
FIG. 4 illustrates an exemplary catheter for use with the connector of FIGS. 2A and 2B, wherein the catheter includes a seal.

(the end that attaches to the pump 200) may include a seal 21 attached thereto, as illustrated in FIG. 4 and described in greater detail below.

The connector 100 may further include a tubular housing 102 having an interior surface defining a lumen and an exterior surface, wherein the housing 102 is configured to at least partially surround one or both of the stem 202 and a proximal end portion of the catheter, e.g., the seal 21. A locking member, e.g., pin 104, as shown in FIGS. 2A-2B, may also be provided. When the stem 202 is adequately engaged with the catheter 20 and connector 100, the pin 104 may be moved, relative to one or more lock openings 103, from an unlocked position (see FIG. 2A), to a locked position (see FIG. 2B). Lock openings 103 may extend generally from the exterior surface of the housing 102 to the interior surface of the housing. The lock openings 103 may form at least one receiving slot 118 that is configured to accommodate a locking leg of the locking member, whereby the locking member (e.g., pin 104) engages a groove 206 formed in the stem 202, axially securing the catheter and connector relative thereto when the locking member is in the locked position. The optional cover member or boot 106, configured to at least partially surround the housing 102, may then be placed, e.g., slid, over the housing 102 as shown in FIG. 2B. The cover member 106 may be configured to reduce stress on surrounding tissue by providing a relatively smooth transition surface around the connector. It may also limit tissue growth into the connector components.

Figure 3:
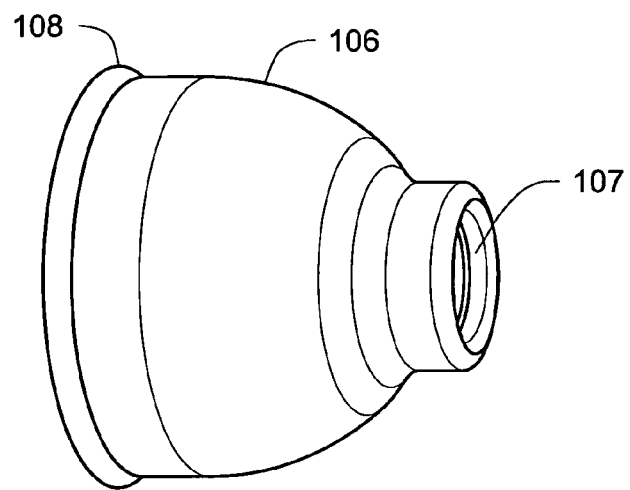
FIG. 3 illustrates an exemplary flexible cover member for use with the connector of FIGS. 2A and 2B.

FIG. 3 is an enlarged perspective view of the optional cover member 106. In the illustrated embodiment, the cover member 106 forms a sleeve defining a central opening 107 to receive the catheter 20 (not shown) and the housing 102 (also not shown). The cover member may include features to assist the physician in grasping and sliding the cover member relative to the catheter 20. For example, in the illustrated embodiment, the cover member includes a protruding lip 108 that provides a raised surface to assist in manipulation.

The cover member 106 may, in one embodiment, be made of silicone rubber, e.g., white ETR silicone, and may optionally be loaded (e.g., 12.5% Barium Sulfate loaded, 2% Titanium Dioxide loaded) to give the connector a degree of radiopaqueness. The use of silicone rubber provides the connector with certain benefits, e.g., a soft, impact-absorbent exterior. Alternatively, other materials may be used to provide, for example, a desired degree of rigidity to assist in holding a locking member in place.

FIG. 4 illustrates the catheter 20 as it may be configured in an exemplary embodiment of the invention. As described above, the proximal end of the catheter 20 (the end that attaches to the pump 200) may include a seal 21 attached thereto, e.g., via adhesive, press fit, mechanical capture, or the like. Alternatively, the seal 21 could be over-molded with the catheter or otherwise formed as an integral portion thereof.

Suitable materials for the seal 21 may include molded silicone or polyurethane. Preferably, the seal is relatively flexible (as compared to the housing 102 described further below). However, other materials, including those that are more rigid, are certainly possible without departing from the scope of the invention.

In the illustrated embodiment, the seal 21 has a head or flange portion 34 defined by a generally cylindrical surface, and a body portion 32. The flange portion 34 may be substantially normal (perpendicular) to a longitudinal axis of the catheter 20. The body portion 32 may be defined by a conical or tapered surface extending from the flange portion. The catheter 20 may extend through the body portion 32 and into the flange portion 34 of the seal. A seal lumen 36, which may also be tapered, may extend from a face 38 of the seal 21 to a lumen 22 of the catheter 20. As a result, when the seal 21 is coupled to the stem 202 (see FIG. 7B) as further described below, the lumen 22 of the catheter 20 is in fluid communication with an infusate output of the pump 200.

The flange portion 34 of the seal 21 may form a contact surface 40 opposite the face 38. The contact surface 40 may abut or contact an abutting surface located on an interior surface of the tubular housing 102, as further described below, when the connector 100 is correctly placed.

FIGS. 5A-5D illustrate various views of the exemplary housing 102 of the connector illustrated in FIGS. 2A-2B. As shown in FIGS. 5A-5D, the housing 102 may form a generally bell-shaped component that may slide over the catheter 20 and seal 21, and at least partially surround and hold the catheter and seal in place relative to the stem 202 of the pump 200.

Figure 5A:
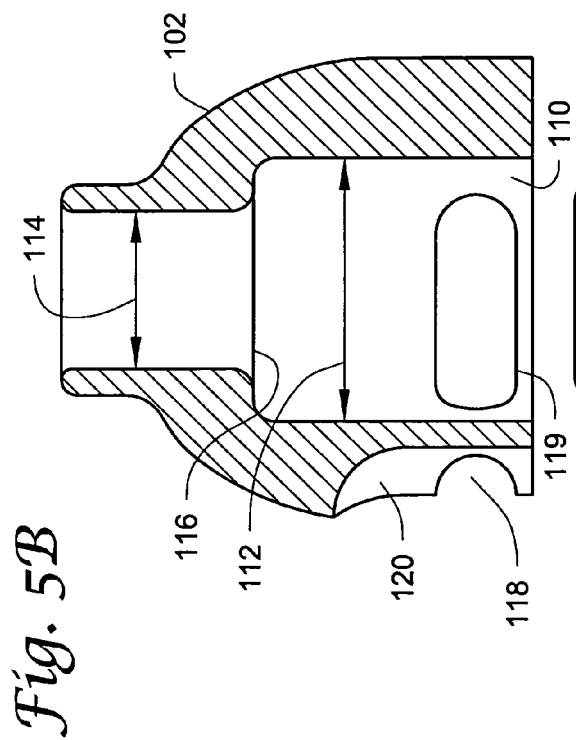
Figure 5B:
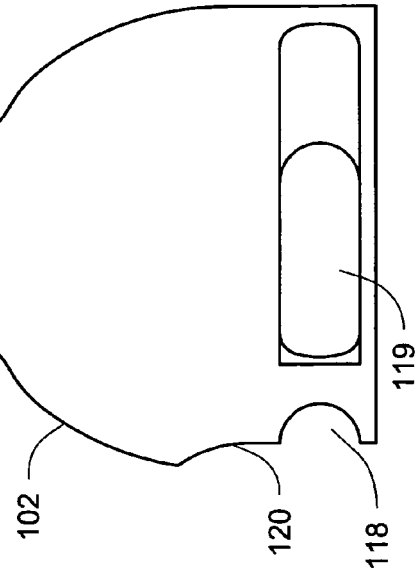
Figure 5C:
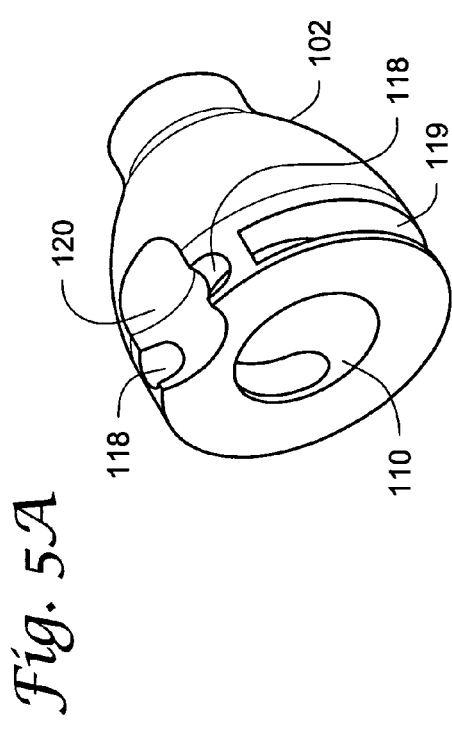
Figure 5D:
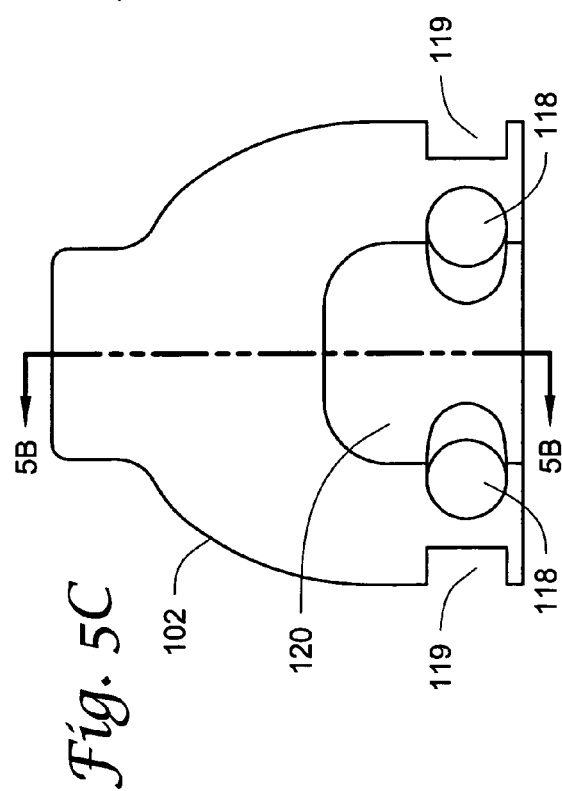

FIG. 5A illustrates a perspective view of the housing 102. A stepped lumen 110 (visible in FIG. 5B) may extend through the housing, wherein the lumen includes a first inner diameter 112 and a second inner diameter 114. The first and second inner diameters correspond generally to the outer diameters of the flange portion 34 and body portion 32 of the seal 21, respectively. The transition between the two diameters may form an abutting surface 116 that selectively abuts the contact surface 40 of the flange portion 34, as further described below.

The housing 102 may also include one or more lock openings which may take the form of passageways, cutouts, or receiving slots 118 (the latter shown in FIGS. 5A-5D) configured to accommodate the locking member. In the illustrated embodiment, two receiving slots 118 are provided in the housing 102 (see e.g., FIG. 5C) to accommodate two locking legs which may together form a substantially U-shaped locking member (e.g., pin 104). However, other locking member configurations may dictate slot geometries that vary from that illustrated herein. The receiving slots 118 may be positioned such that they form windows 119 in the housing to accommodate movement of pin 104, as further described below.

To simplify removal of the pin 104, the housing may further include a scoop or depression 120. The receiving slots 118 and the depression 120 are shown in more detail in FIGS. 5C and 5D.

As with other connector components described herein, the housing 102 may be formed from various bio-compatible materials. For example, the housing may be made, e.g., machined or molded, from a material that is relatively rigid compared to the seal 21. Materials such as titanium, stainless steel, and rigid plastic are contemplated.

Figure 6A:
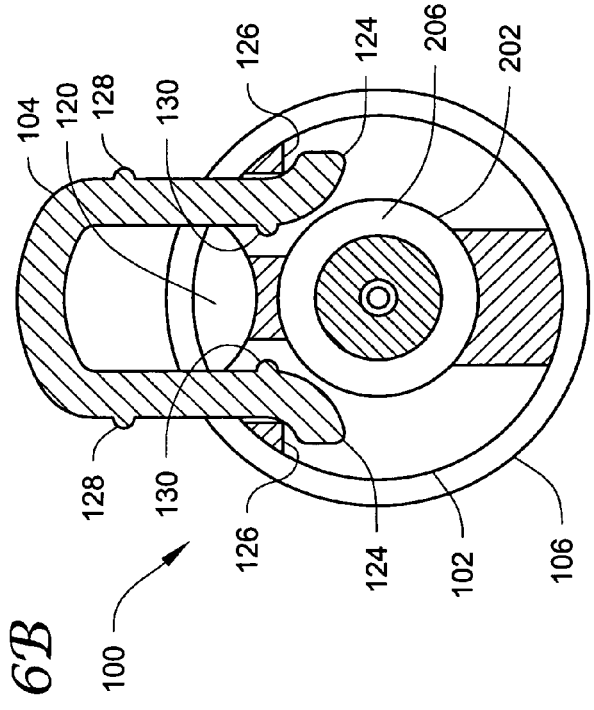
Figure 6B:
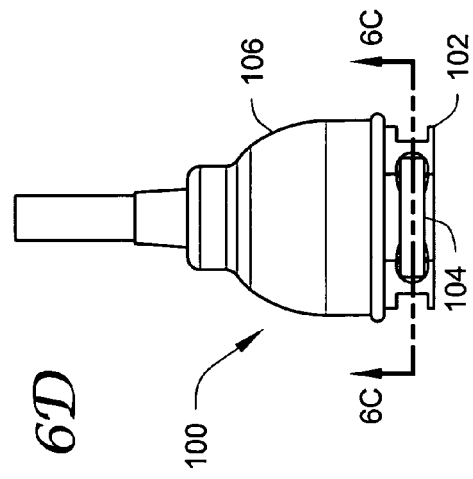
Figure 6C:
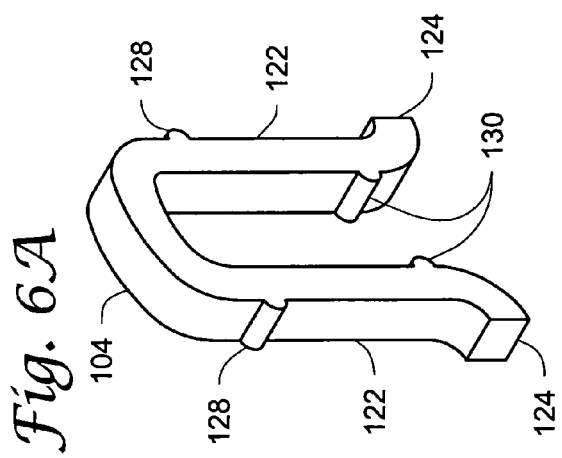

FIGS. 6A-6D illustrated an exemplary locking member, e.g., a resilient U-shaped pin 104. The pin 104 may include locking legs 122 (see FIG. 6A) configured to move within the receiving slots 118 (see FIG. 5A). The legs 122, when moved into the locked position, may each define a secant with respect to a cross section of the lumen 110 of the housing 102. As a result, the legs may engage the stem 202 as shown in FIG. 6C. Further, each leg 122 may include a protruding foot 124 (see FIGS. 6A-6C) that engages the window 119 (see FIGS. 5A-5D). The foot 124 may assist in guiding the pin 104 during movement. Moreover, the foot 124 may contact stop portions 126 located on the interior surface of the housing 102 as the pin 104 is withdrawn from the receiving slot (see FIG. 6B), thereby limiting or preventing the pin from separating from the housing once the pin and housing are assembled (e.g., the pin may be captivated by the receiving slot).

Figure 6D:
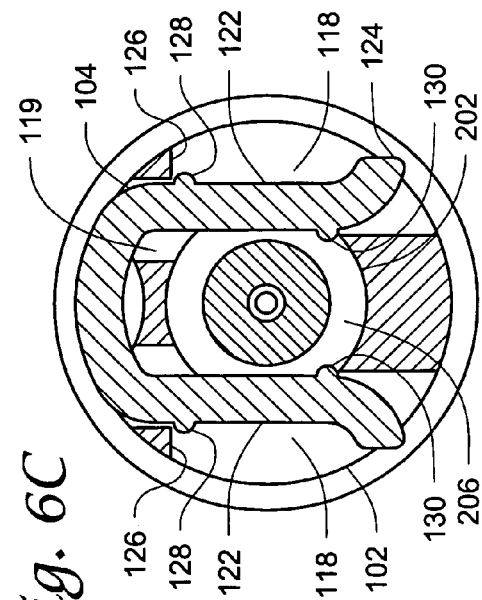

In the illustrated embodiment, the pin 104 may also include one or more first lock tabs 128 and one or more second lock tabs 130 that assist in maintaining or securing the pin 104 in the locked position (see FIGS. 6C and 6D). For example, once the connector 100 is coupled to the stem 202 of the pump 200, the pin 104 may be moved from the unlocked position of FIG. 6B to the locked position of FIG. 6C. When in the locked position, the legs 122 of the pin 104 engage the groove 206 of the stem 202, thereby securing the connector 100 to the stem. To maintain the pin in the locked position, the first lock tabs 128 are configured to contact the stop portions 126 of the housing 102 when the pin is moved from the locked position. Similarly, the second lock tabs 130 are configured to contact the stem 202 when the pin 104 is moved from the locked position. As a result, the first and second lock tabs may assist in keeping the pin 104 from inadvertently moving from the locked position. While illustrated with both first and second lock tabs, alternative embodiments may achieve locking of the pin with only one set of lock tabs, e.g., the first lock tabs 128 or the second lock tabs 130 may be optional.

The pin 104 may move between the unlocked position and the locked position by deflecting sufficiently for the lock tabs 128 and 130 to move past the stop portions 126 and stem 202, respectively. Stated another way, the pin 104 may have snap-fit engagement with the housing 102 and stem 202. As a result, full engagement of the pin 104 may be indicated by tactile or even auditory feedback to the physician.

While the pin 104 may be made from most any bio-compatible material, it is preferably made from a material that provides it with adequate rigidity to remain in the locked position of FIG. 6C. Yet, it is preferably flexible enough to permit the snap-fit interrelation with the housing 102 and the stem 202. Suitable materials may include titanium, stainless steel, and rigid plastic. Various manufacturing techniques, e.g., photo-etching, machining, etc., may be used to make the pin 104.

FIGS. 7A and 7B illustrate the connector 100 as it may be used to connect the catheter 20 to the pump stem 202 (the latter shown only in FIG. 7B), wherein the connector is shown in the locked configuration with a cover member covering the housing. With reference to FIG. 7B, the pin 104 is shown with the legs 122 engaged with the groove 206 of the stem 202. When the pin 104 is so engaged, the tip of the stem 202 preferably extends into the catheter 20 to form a substantially leak-free seal directly therewith. Moreover, the abutting surface 116 of the housing 102 is preferably positioned to abut the contact surface 40 of the seal 21. As a result, the flange portion 34 of the seal 21 is biased against the stem 202 to form a compression seal. Moreover, the second inner diameter 114 (see FIG. 5B) of the housing 102 and the opening 107 (see FIG. 3) of the cover member 106 may engage the tapered surface of the body portion 32 with interference fit. However, in other embodiments, these components may provide a clearance fit.

While the connector assemblies illustrated herein may be scaled for use with most any size catheter, an exemplary infusion pump/catheter connector as shown herein may utilize a catheter 20 having an outer diameter of about 1 mm. In such a case, the largest outermost diameter of the housing 102 may be about 9.5 mm, while the first inner diameter 112 of the housing (see FIG. 5B) is about 5 mm, and the second inner diameter 114 is about 3.5 mm. Moreover, the pin 104 may have a thickness of about 1.3 mm, an overall height of about 8 mm, and a width of about 7.3 mm. The overall volume of the connector 100 may be less than about 1 cubic centimeter (cc), e.g., less than about 0.95 cc.

Figure 8A:
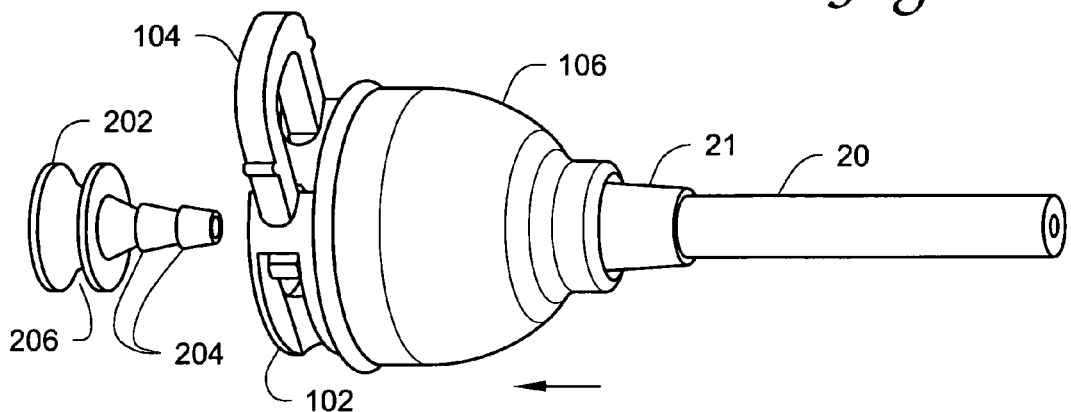
Figure 8B:
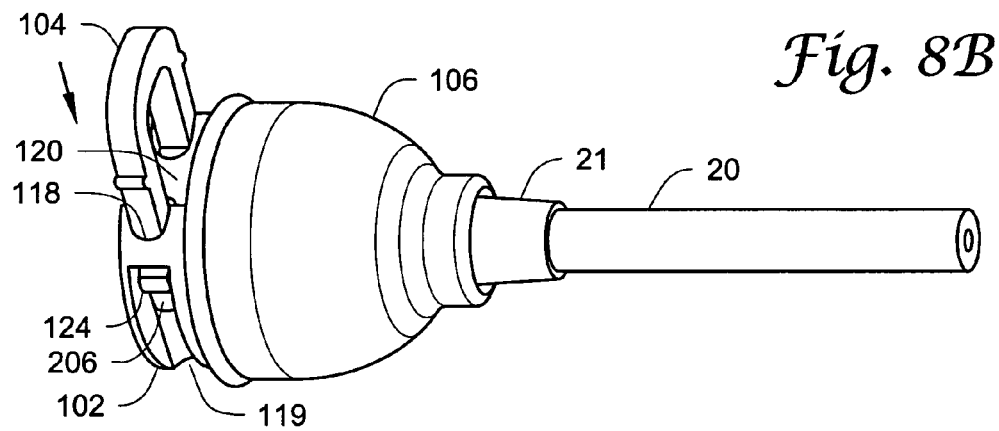
Figure 8C:
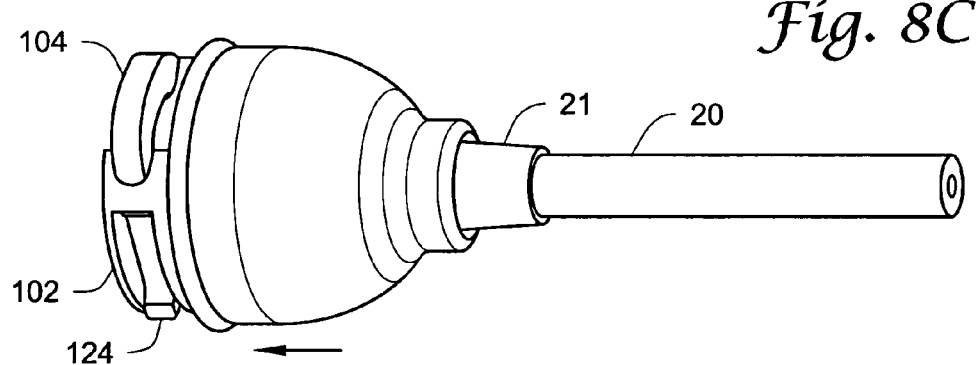
Figure 8D:
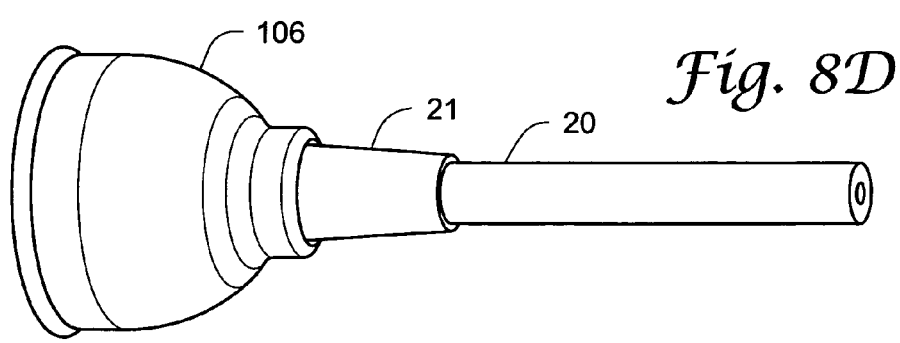

FIGS. 8A-8D illustrate an exemplary method for coupling the catheter 20 to the stem 202 using the connector 100. The pin 104 may be assembled with the housing 102 and the housing slid over the distal end of the catheter 20 prior to implantation. The housing 102 may be slid over the seal 21 until the abutting surface 116 located on the interior surface of the tubular housing (see FIGS. 5B and 7B) abuts the contact surface 40 of the flange portion of the seal (see FIGS. 4 and 7B). With the pin 104 in its unlocked position as shown in FIG. 8A, the connector 100 may be moved towards the stem 202 until the pin 104 aligns with the groove 206 as indicated in FIG. 8B, wherein the mating of the abutting surface 116 with the contact surface 40 may compress the seal. The pin 104 may then be moved (e.g., by translating the legs 122 (see FIG. 6A) relative to the lock opening 118 of the housing) by the physician from the unlocked position to the locked position, the latter shown in FIG. 8C (and FIG. 6C). The pin 104 is, preferably, moved into the locked position without the use of tools. Once the pin 104 is moved to the locked position, the catheter is secured to the pump. At this point, the optional cover member 106 may be moved axially towards the pump until it substantially covers the housing 102 as shown in FIG. 8D (and FIG. 7B).

To remove the catheter 20 from the pump 200, the cover member may be slid away from the housing 102, and the pin 104 may be moved to the unlocked position illustrated in FIG. 8B. To grasp the pin 104, a prying force may be applied, e.g., with tools commonly found in the operating room, between the pin 104 and the housing 102 (in the vicinity of the depression 120). Once the pin 104 is moved to the unlocked position, the connector may be pulled away from the pump 200 with minimal pulling force. The force necessary to remove the pin 104 is preferably between about 1 and about 5 pounds (lbf).

An alternative embodiment of the present invention is illustrated in FIGS. 9A-9D. As shown in FIGS. 9A and 9B, a connector 300 may be provided that includes a tubular housing 302 having an interior surface (defining a lumen) and an exterior surface. A locking member may also be included. In the illustrated embodiment, the locking member may include one or more locking legs, e.g., a pair of locking wings 304 as shown in FIGS. 9B and 9D, which may be pivotally attached to the housing 302, e.g., via hinge holes 368. As illustrated in FIG. 9B, the locking wings 304 may include hinge holes 368 at each end so that the identical locking wing may be used on both sides of the housing.

The housing 302, as shown in FIGS. 9A and 9B, may include a pair of lock openings 303 each configured to accommodate one of the locking wings 304. When the stem 202 is adequately engaged with the catheter 20 and connector 300, the locking wings 304 may be moved (e.g., pivoted relative to the lock opening of the tubular housing) from an unlocked position, wherein the locking wing is located at or beyond the interior surface of the tubular housing (see FIG. 9B) to a locked position, wherein the locking wing protrudes inwardly past the interior surface and into the lumen of the tubular housing (see FIGS. 9A, 9C, and 9D). In the locked position, the wings 304 may engage the groove 206 formed in the stem 202 and axially secure the catheter and connector relative thereto. Alternatively, the locking wings 304 may be moved into the locked position prior to engaging the stem 202 with the catheter 20 and connector 300 (e.g., prior to inserting the stem of the device into the housing).

A cover member 306, as shown in FIGS. 9C and 9D, may be slid axially over the housing 302, either prior to or after inserting the stem of the device into the housing, to hold the locking wings 304 in the locked position (e.g., to bias the locking legs to the locked position). In other embodiments, alternative biasing mechanisms (e.g., springs) may hold the locking wings 304 in the locked position. The cover member 306 may assist in providing a visual and/or tactile cue to the physician that the catheter is secured to the stem of the medical device.

As the cover member 306 may hold the locking wings 304 in the locked position, it may be desirable to form the cover member 306 of a material that is somewhat more rigid as compared with material selected for cover member 106 of connector 100. In addition, the cover member 306 may include a textured surface (e.g., ridges 308) which the physician may use to grip and axially move the cover member 306 from an uncovered position (not shown) to a covered position (e.g., FIGS. 9C and 9D).

The locking wings 304 are preferably captively held by the housing 302, such as in the pivotal fashion illustrated in FIG. 9B. The inner edges of each locking wing 304 may further include an angled face 309. When in the locked position, an outer edge 359 of each locking wing 304 generally corresponds in shape and position to the exterior surface in the housing 302 so that a substantially smooth, even exterior surface of the housing 302 as shown in FIGS. 9A and 9D is provided. That is, when in a securely locked position, the locking wings do not substantially protrude beyond the exterior surface of the housing 302. Alternatively, the wings 304, e.g., outer edges 359, may protrude slightly beyond the housing envelope to permit greater biasing by the cover member 306. When in the locked position, the locking wings 304 may be prevented from over-compressing the stem 202 by, e.g., forming a stop surface 360 in the lock openings 303, as illustrated in FIG. 9B.

The locking wings 304 may be made from most any biocompatible material. It is, however, preferable that the locking wings 304 are made from a material that provides adequate rigidity for the locking wings 304 to remain in the locked position (FIGS. 9C and 9D). Suitable materials may include titanium, stainless steel, and rigid plastic.

FIGS. 9C and 9D illustrate the connector 300 coupling the catheter 20 to stem 202 of the medical device (not shown), wherein the connector is shown in the locked configuration. With reference to FIG. 9D, the locking wings 304 are shown engaged with the groove 206 of the stem 202. When the locking wings 304 are in the locked position, the tip of the stem 202 preferably extends into the catheter 20 to form a substantially leak-free seal directly therewith. In addition, housing 302 may include an abutting surface 376 (preferably normal to the longitudinal axis of the catheter 20) that is preferably positioned to abut the contact surface 40 of the seal 21. As a result, the flange portion 34 of the seal 21 may be biased against the stem 202 to form a compression seal. Moreover, as illustrated in FIG. 9D, the housing 302 and the cover member 306 may engage the tapered surface of the body portion 32 with either a clearance or an interference fit.

To attach the catheter 20 to the stem 202 of a medical device using the connector 300 of FIGS. 9A-9D, the housing 302 may first be slid over the seal 21 from the distal end of the catheter until the abutting surface 376 of the housing abuts the contact surface 40 of the seal. The locking wings 304, pivotally connected to the housing 302, may then be pivotally moved, relative to the lock openings 303 of the housing 302, into the locked position, and the optional cover member 306 axially slid over the tubular housing 302. The cover member 306 may bias the locking legs (e.g., locking wings 304) to the locked position. The connector 300 may then be moved toward the stem 202 until the angled surface 309 of the locking wings is forced over a lip 205 of the stem 202 (see FIG. 9B). The cover member 306 may deflect to permit pivoting of the locking wings 304 as they cam over the lip 205. Once the locking wings 304 reach the groove 206, the cover member 306 may bias the locking wings 304 into the groove 206 in a "snap-fit"-like manner. Alternatively, the cover member 306 may be moved into place after the locking wings 304 are engaged with the groove 206.

The positioning of the locking wings 304 in the groove 206 may be performed without the use of tools. Once the connector 300, provided to the stem 202 in the locked configuration, is forced over the stem and the locking wings 304 are seated in the groove 206, the catheter 20 is generally secured to the pump 200. To disconnect the catheter 20 from the pump 200, the cover member 306 may be slid away from the housing 302, and the locking wings 304 moved to the unlocked position by, e.g., pivoting them outwardly from the housing 302 as illustrated in FIG. 9B. The connector 300 may then be pulled away from the stem 202.

Embodiments of the present invention provide a relatively low-profile catheter/pump connector and connection systems for connecting medical tubing (e.g., catheters/catheter assemblies) to medical devices, such as implantable infusion pumps. These connectors may be intuitively locked and unlocked without tools (or with tools that are readily available in a surgical environment). Moreover, the components of the connectors may preferably be captivated, reducing the risk of lost or misplaced parts. Further, embodiments of the present invention may provide the physician or clinician with both auditory and/or tactile feedback when the catheter is secured to the medical device.

Still further, connectors in accordance with embodiments of the present invention provide desirable resistance to catheter separation when subjected to anatomically-induced pulling forces, yet may be unlocked to permit physician removal with application of minimal forces.

Illustrative embodiments of this invention are discussed and reference has been made to possible variations within the scope of this invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below, and equivalents thereof.

What is claimed is:

1. A connector for removably coupling a catheter to a medical device, the connector comprising:

a tubular housing comprising an exterior surface and an interior surface, wherein the interior surface defines a lumen configured to receive both a proximal end portion of the catheter and a stein of the medical device, and further wherein a lock opening extends through the housing between the exterior surface and the interior surface;

a locking member comprising a locking leg pivotally attached to the housing and operable to pivot, relative to the lock opening, about a pivot axis that is parallel to a longitudinal axis of the lumen between an unlocked position, wherein the locking leg is located at or beyond the interior surface, and a locked position, wherein the locking leg protrudes inwardly past the interior surface and into the lumen of the housing, the locking leg defining a secant with respect to a cross section of the lumen of the housing when the locking member is in the locked position; and a cover member configured to surround the housing and the locking member when the locking member is in the locked position.

2. The connector of claim 1, wherein the locking member engages a groove formed in the stem of the medical device when the locking member is in the locked position.

3. The connector of claim 1, wherein the proximal end portion of the catheter comprises a seal.

4. The connector of claim 3, wherein the seal comprises a flange portion comprising a contact surface configured to contact an abutting surface located on the interior surface of the housing.

5. The connector of claim 4, wherein the seal further comprises a body portion extending from the flange portion.

6. The connector of claim 5, wherein the body portion of the seal comprises a tapered outer surface.

7. The connector of claim 3, wherein the housing is configured to at least partially surround the seal.

8. The connector of claim 3, wherein the seal is attached to the catheter with an adhesive.

9. The connector of claim 3, wherein the seal is molded to the catheter.

10. The connector of claim 1, wherein the cover member is radiopaque.

11. The connector of claim 1, wherein the locking member comprises two locking legs.

12. The connector of claim 1, wherein the medical device comprises an implantable infusion pump.

13. A connection system for coupling a catheter to a stem of a medical device, the system comprising:
    a catheter assembly comprising a length of medical tubing and a seal attached at or near a proximal end of the medical tubing, the seal comprising:
        a flange portion comprising a contact surface, the flange portion substantially normal to a longitudinal axis of the medical tubing; and
        a tapered body portion extending from the flange portion of the seal;
    a tubular housing comprising an exterior surface and an interior surface, wherein the interior surface defines a lumen configured to surround both the flange portion of the seal and the stem of the medical device, and further wherein a lock opening extends through the housing between the exterior surface and the interior surface;
    a locking member comprising a locking leg pivotally attached to the housing and operable to pivot, relative to the lock opening, between an unlocked position, wherein the locking leg is located at or beyond the interior surface, and a locked position, wherein the locking leg protrudes inwardly past the interior surface and into the lumen of the housing such that the locking leg defines a secant with respect to a cross section of the lumen of the housing when the locking member is in the locked position, the locking leg configured to engage a groove formed in the stem of the medical device to axially restrict movement of the housing relative to the stem; and
    a cover member configured to at least partially surround the housing when the locking member is in the locked position.

14. The connection system of claim 13, wherein the medical device is an implantable infusion pump.

15. The connection system of claim 13, wherein the cover member surrounds the lock opening of the housing when the locking member is in the locked position.

16. A connection system for coupling a catheter to a medical device, the system comprising:
    a catheter assembly comprising a length of medical tubing and a seal attached at or near a proximal end of the medical tubing, the seal comprising a flange portion having a contact surface normal to a longitudinal axis of the medical tubing;
    a tubular housing comprising an exterior surface and an interior surface, wherein the interior surface defines a lumen configured to receive and surround both the flange portion of the seal and a stem of the medical device, the interior surface comprising an abutting surface configured to abut the contact surface of the flange portion of the seal, and further wherein two lock openings extend through the housing between the exterior surface and the interior surface; and
    a locking wing pivotally attached to the housing at each lock opening, each locking wing operable to pivot, relative to its corresponding lock opening, from an unlocked position to a locked position, wherein, when in the locked position, each locking wing: defines a secant with respect to a cross section of the lumen of the housing; and is configured to engage a groove formed in the stem to hold the flange portion of the seal in axial compression against a face of the stem.

17. The connection system of claim 16, wherein the proximal end of the medical tubing defines an opening configured to receive a portion of the stem.

18. The connection system of claim 16, further comprising a cover member configured to surround the lock openings of the housing when the locking wing is in the locked position.

* * * * *

UNITED STATES PATENT AND TRADEMARK OFFICE
CERTIFICATE OF CORRECTION

| | | |
|---|---|---|
| PATENT NO. | : 7,678,101 B2 | Page 1 of 1 |
| APPLICATION NO. | : 11/393089 | |
| DATED | : March 16, 2010 | |
| INVENTOR(S) | : Shahn S. Sage | |

It is certified that error appears in the above-identified patent and that said Letters Patent is hereby corrected as shown below:

Col. 10, Line 50: "a stein of" should read --a stem of--.

Signed and Sealed this
Sixth Day of September, 2011

David J. Kappos
*Director of the United States Patent and Trademark Office*